(12) United States Patent
Patodia et al.

(10) Patent No.: US 12,337,008 B2
(45) Date of Patent: Jun. 24, 2025

(54) NUTRACEUTICAL FORMULATION FOR POLYCYSTIC OVARY SYNDROME

(71) Applicants: Ramesh Patodia, Mumbai (IN); Sonal Chauhan, Mumbai (IN)

(72) Inventors: Ramesh Patodia, Mumbai (IN); Sonal Chauhan, Mumbai (IN)

( * ) Notice: Subject to any disclaimer, the term of this patent is extended or adjusted under 35 U.S.C. 154(b) by 718 days.

(21) Appl. No.: 17/527,581

(22) Filed: Nov. 16, 2021

(65) Prior Publication Data

US 2022/0072018 A1  Mar. 10, 2022

Related U.S. Application Data

(63) Continuation-in-part of application No. PCT/IN2020/000019, filed on Sep. 16, 2020.

(30) Foreign Application Priority Data

Sep. 20, 2019 (IN) .............................. 201921037938

(51) Int. Cl.

| | |
|---|---|
| *A61K 31/7004* | (2006.01) |
| *A23L 33/00* | (2016.01) |
| *A23L 33/125* | (2016.01) |
| *A23L 33/155* | (2016.01) |
| *A23L 33/16* | (2016.01) |
| *A23L 33/175* | (2016.01) |
| *A23L 33/185* | (2016.01) |
| *A23L 33/22* | (2016.01) |
| *A61K 31/07* | (2006.01) |
| *A61K 31/197* | (2006.01) |
| *A61K 31/198* | (2006.01) |
| *A61K 31/375* | (2006.01) |
| *A61K 31/4188* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/555* | (2006.01) |
| *A61K 31/59* | (2006.01) |
| *A61K 31/675* | (2006.01) |
| *A61K 31/733* | (2006.01) |
| *A61K 33/04* | (2006.01) |
| *A61K 33/06* | (2006.01) |
| *A61K 33/10* | (2006.01) |
| *A61K 33/14* | (2006.01) |
| *A61K 33/18* | (2006.01) |
| *A61K 33/26* | (2006.01) |
| *A61K 33/30* | (2006.01) |
| *A61K 33/32* | (2006.01) |
| *A61K 38/16* | (2006.01) |
| *A61P 5/28* | (2006.01) |

(52) U.S. Cl.

CPC ........ *A61K 31/7004* (2013.01); *A23L 33/125* (2016.08); *A23L 33/155* (2016.08); *A23L 33/16* (2016.08); *A23L 33/175* (2016.08); *A23L 33/185* (2016.08); *A23L 33/22* (2016.08); *A23L 33/40* (2016.08); *A61K 31/07* (2013.01); *A61K 31/197* (2013.01); *A61K 31/198* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/555* (2013.01); *A61K 31/59* (2013.01); *A61K 31/675* (2013.01); *A61K 31/733* (2013.01); *A61K 33/04* (2013.01); *A61K 33/06* (2013.01); *A61K 33/10* (2013.01); *A61K 33/14* (2013.01); *A61K 33/18* (2013.01); *A61K 33/26* (2013.01); *A61K 33/30* (2013.01); *A61K 33/32* (2013.01); *A61K 38/168* (2013.01); *A61P 5/28* (2018.01); *A23V 2002/00* (2013.01)

(58) Field of Classification Search

CPC .......................... A61K 31/7004; A23L 33/125
See application file for complete search history.

(56) References Cited

U.S. PATENT DOCUMENTS

2016/0235822 A1\*  8/2016  Holstein ............ A61K 31/4415
2019/0125675 A1\*  5/2019  Fioretti .................. A23L 33/125

FOREIGN PATENT DOCUMENTS

WO    WO-2019057709 A1 \*  3/2019  ........... A61K 31/519

OTHER PUBLICATIONS

Hariprasath G, Sakila S, Lavanya Kumari K, Sethupathy S, Taurine Supplementation Improves Insulin Sensitivity and Lipid Profile in PCOS Women, International Journal of Scientific Research, vol. 7, Issue 1, Jan. 2018, ISSN No. 2277-8179, IF 4.176, IC Value 93-98.

Williams T, Mortada R, Porter S, Diagnosis and Treatment of Polycystic Ovary Syndrome, American Family Physician, 94(2):106-113(2016).

(Continued)

*Primary Examiner* — Michael B. Pallay
(74) *Attorney, Agent, or Firm* — Jyoti C Iyer

(57) ABSTRACT

Nutraceutical food supplement for treatment of young women in post-puberty age suffering from polycystic ovary syndrome with symptoms like irregular menstruation cycles, insulin resistant diabetes, infertility, hair loss, acne and weight gain is provided. Formulations having myo-inositol and its D-chiro isomer along with plant proteins, a carbohydrate (inulin) and other plant fibres; along with well-defined proportions of vitamins (A, $B_{1\ to\ 6}$; $B_{12}$ and C); several minerals like Ca, Cr, Fe, K, Mg, Mn, Na and Zn and essential amino acids like L-Glutamine, L-Lysine, and L-Taurine are provided.

4 Claims, No Drawings

(56) References Cited

Faghfoori Z, Fazelian S, Shadnoush M, Goodarzi R, Nutritional Management in Women with Polycystic Ovary Syndrome: A Review Study, Diabetes & Metabolic Syndrome: Clinical Research Reviews, http://dx.doi.org/10.1016/j.dsx.2017.03.030, 1871-4021, S429-S432(2017), Diabetes India.

Regidor P-A and Schindler AE, Myoinositol as a safe and alternative approach in the Treatment of Infertile PCOS Women: A German Observational Study, International Journal of Endocrinology, vol. 2016, Article ID 9537632, 5 pages, http//dx.doi.org/10.1155/2016/9537632.

Gunalan E, Yaba A, Yilmaz B, The Effect of Nutrient Supplementation in the Management of Polycystic Ovary Syndrome-Associated Metabolic Dysfunctions, Journal od the Turkish-German Gynecological Association, 19:220-232(2018), DOI: 10.4274/jtgga.2018.0077.

Kazemi M, McBreairty Le, Chizen DR, Pierson RA, Chilibeck PD, Zello GA, A Comparison of a Pulse-Based Diet and the Therapeutic Lifestyle Changes Diet in Combination with Exercise and Health Counselling on the Cardio-Metabolic Risk Profile in Women with Polycystic Ovary Syndrome: A Randomized Controlled Trial, Nutrients, 10:1387(2018); doi:10.3390/nu101387.

Two (2) pages of International Search Report in International Application No. PCT/IN2020/000019 mailed Dec. 30, 2020.

Turner-McGrievy GM et al., Low Glycemic Index Vegan or Low Calorie Weightloss Diets for Women with Polycystic Ovary Syndrome: A randomized Controlled Feasibility Study, Nutrition Research, 34(6):552-558(2014), doi:10.1016/j.nutres.2014.04.Oil.

\* cited by examiner

NUTRACEUTICAL FORMULATION FOR POLYCYSTIC OVARY SYNDROME

This application is a by-pass continuation-in-part of International Application Serial No. PCT/IN2020/000019, filed Sep. 16, 2020, which claims priority to Indian Application Serial No. 201921037938, filed Sep. 20, 2019, all of which are incorporated by reference in entirety.

FIELD

A nutrient food supplement for treatment of insulin resistant Polycystic Ovary Syndrome (PCOS).

BACKGROUND

Polycystic Ovary Syndrome (PCOS) is a metabolic imbalance defined by a several symptoms frequently seen in women during their post-puberty age. The major symptoms that the person experiences can be very different from one to other. If there be two or more of the symptoms mentioned herein, the person needs a thorough check-up to determine the treatment modality. The common symptoms of PCOS are: (i) irregular or missing menstrual cycle; (ii) infertility; (iii) excess unwanted body or facial hair growth; (iv) thinning of hair on the scalp; (v) often weight gain around the waist; (vi) skin problems including skin tags, skin darkening and (vii) appearance of acne. The root cause of PCOS being still unknown, the contributory factors are known to be stress, diets, genetic disposition, pollution, excess insulin production and low grade inflammation. The symptoms of PCOS being multi-facetted, the presently practiced treatment is mostly symptomatic like use of fertility and birth control pills to regulate menstruation, insulin sensitizing metformin and isomers of inositol (myo- and d-Chiro) and topical anti-hair growth creams and medication. Emphasis is laid also on life style modifications and specialized restricted dietary regimens for weight control of PCOS patients.

Polycystic Ovary Syndrome (PCOS) is a hormonal disorder normally occurring in post-puberty women of reproductive age group. In such cases, when there occurs a hormonal imbalance and the levels of male hormone androgen becomes high in women it gets stored in small globules inside the ovary which finally results in a cystic formation. Hence it is named as Polycystic Ovary Syndrome (PCOS) or polycystic ovary Disorder (PCOD).

The excess production of male hormones in women leads to growth of unwanted hair on face or other parts of body that is normally not seen in women. It also causes thinning or loss of hair on the scalp, crates acne and leads to hypertension and insulin resistant diabetes. The imbalance due to lower level in female hormone (progesterone) causes irregularities in the menstruation cycle; reduces chances of pregnancy and leads to total infertility. Such women also tend to gain weight around the waist.

Unfortunately, no single root cause of PCOS is identified till date and only the symptomatic treatments are presently prescribed. For instance, metformin and a combination of inositol isomers have been recommended for treatment of infertility, hair growth inhibiting topical creams are advised and hair transplant for overcoming hair thinning on scalp are recommended and are being tried. Life-style changes and strict dietary regimens are suggested for weight gain and diabetes.

Studies found that when inositol alone was administered about 62% of patients showed improvement in ovulation (*Gynecol Endocrinol.* 2015 Feb.; 31(2):131-5. doi: 10.3109/09513590.2014.964640, Epub 2014 Sep. 26, Zdravko Kamenov 1, Georgi Kolarov, Antoaneta Gateva, Gianfranco Carlomagno, Alessandro D Genazzani).

Other studies found that administering inositol and folic acid resulted in about 70% restoration of ovulation (*Int J Endocrinol.* 2016; 2016: 9537632, Published online 2016 Aug. 23. doi: 10.1155/2016/9537632, PMCID: PMC5011528, PMID: 27642297 Myoinositol as a Safe and Alternative Approach in the Treatment of Infertile PCOS Women: A German Observational Study, Pedro-Antonio Regidor and Adolf Eduard Schindler.)

In an exhaustive randomized Clinical trial (Phase –4) with 46 young women suffering from PCOS and hyper-insulemia the beneficial effect of drugs like m-inositol, d-chiro inositol plus folic acid has been studied. (https://clinicaltrials.gov/ct2/show/NCT01626443; Role of Myo-inositol and D-chiro Inositol on the Ovaric and Metabolic Functions).

SUMMARY OF THE INVENTION

Disclosure provides a nutraceutical composition having a protein and an inositol.

Some embodiments of the nutraceutical composition include folic acid. Some embodiments of the nutraceutical composition include a folate. Some embodiments of the nutraceutical composition include a vitamin or a vitamin like substance. Some embodiments of the nutraceutical composition include a mineral. Some embodiments of the nutraceutical composition include a fiber. Some embodiments of the nutraceutical composition include an essential amino acid.

In some embodiments of the nutraceutical composition, the protein is a protein of plant origin, a protein of animal origin or combinations thereof.

In some embodiments of the nutraceutical composition the protein of plant origin is a pea protein, a rice protein or combinations thereof.

In some embodiments of the nutraceutical composition the inositol is selected in the group consisting of myoinositol, d-chiro inositol or combinations thereof.

In some embodiments of the nutraceutical composition, the vitamin is selected from the group consisting of vitamin A, vitamin B1, vitamin B2, vitamin B3, vitamin B4, vitamin B5, vitamin B6, vitamin C, vitamin D or combinations thereof.

In some embodiments of the nutraceutical composition, the vitamin like substance is selected from the group consisting of biotin, folic acid or combinations thereof.

Some embodiments of the nutraceutical composition include a dose of a vitamin or vitamin like substance at a dosage as per recommendation by the Indian council of Medical Research for a healthy normal person. In some embodiments the healthy normal person is a woman of post-puberty age.

In some embodiments of the nutraceutical composition the mineral is selected from the group consisting of calcium, chromium, iron, potassium, magnesium, manganese, sodium, zinc, or combinations thereof. In some embodiments of the nutraceutical composition, a chemical form of the mineral is selected from the group consisting of chloride, sulfate, carbonate, or combinations thereof. In some embodiments of the nutraceutical formulation, a dose of the mineral is as per recommendation by the Indian council of Medical Research for a healthy normal person. In some embodiments the healthy normal person is a woman of post-puberty age.

In some embodiments of the nutraceutical composition the fiber is inulin. In some embodiments, other vegetables provide sources of fiber.

In some embodiments of the nutraceutical composition the essential amino acid is selected from the group consisting of L-glutamine, L-lysine, L-taurine or combinations thereof. In some embodiments of the nutraceutical composition a dose of the essential amino acid is as per recommendation by the Indian council of Medical Research for a healthy normal person. In some embodiments the person is a woman of post-puberty age.

In some embodiments, the nutraceutical composition includes:
about 10% to about 43.5% protein;
about 10% to about 65% plant fiber;
about 1% to about 3% inositol;
less than about 1% vitamins; and
less than about 1% minerals.

In some embodiments, the nutraceutical composition includes:
about 43.5% protein;
about 65% plant fiber;
about 2% inositol;
about 1% vitamins; and
about 1% minerals.

Some embodiments provided a method of treating insulin resistance diseases by administering the disclosed nutraceutical composition to a subject in need thereof. Insulin resistance diseases are caused by metabolic imbalances.

In some embodiments of the method of treating insulin resistance diseases, the insulin resistance disease is selected from the group consisting of polycystic ovarian syndrome, diabetes, arthritis hypertension and endothelial dysfunction, hyperlipidemia, atherosclerotic heart disease, obesity, peripheral artery disease, type A syndrome, type B syndrome, Acanthosis *Nigricans*, dyslipidemia or cardiovascular conditions.

In some embodiments of the method of treating insulin resistance diseases, a symptom of the poly cystic ovarian syndrome is selected from the group consisting of irregular or missing menstrual cycle, infertility, excess unwanted body or facial hair growth, thinning of hair on the scalp, weight gain around the waist, skin tags, skin darkening, appearance of acne or combinations thereof.

DETAILED DESCRIPTION OF THE INVENTION

Realizing the limitations in the scientific knowledge on the root cause of PCOS and the multiplicity of its probable causes leading to multiple symptoms and that there is an absence of any single comprehensive treatment of all its symptoms and that only individual symptomatic relief are recommended, has necessitated this research leading to development of a nutraceutical formulation providing a complete and comprehensive nutritional supplement to be taken twice daily with ease and taste by a subject who exhibits symptoms of PCOS. The disclosed formulations have proved to be a single highly efficient remedy for treatment of many of the symptoms of PCOS. While limited success has been achieved in treating infertility with inositol isomers in combination with folic acid and vitamins, the disclosed nutrient supplements significantly enhanced effectiveness in controlling the varied symptoms of PCOS.

Some embodiments provide a nutraceutical formulation of vitamins and vitamin like substances, a host of minerals and essential amino acids and other several such plant materials like leguminous and cereal proteins derived basically from peas and rice, that were found to be working as carriers and/or facilitators of and thereby to act in synergism with inositol isomers in overcoming the maladies of PCOS in particularly insulin resistant post-puberty reproductive age of women. As shown by other studies discussed above, administering inositol alone showed improvement in ovulation in about 62% of patients or in about 70% patients, and our unpublished data showed that administering protein alone showed negligible restoration of ovulation, whereas administering the disclosed formulations resulted in almost 100% restoration of ovulation, which indicates a likely synergistic effect of combination of inositol, protein and other components in the disclosed formulations.

Some embodiments provide nutraceutical formulations that are not a drug but a food supplement containing clinically permissible and regularly used pharmaceuticals in proportions as these exist in a normal women or are normally recommended for use by Indian Council of Medical Research (ICMR). Some embodiments provide a nutraceutical formulation that mainly contains plant based leguminous and cereal proteins derived from pea and rice that is rich in absorbable iron and contains nine essential amino acids. Some embodiments do not provide proteins from peanut, cow's milk, eggs, soya, fish and wheat and thereby none of the food allergens from these sources of protein. Other vegetable sources of protein are millets like jowar and bajra, pulses like Bengal gram, and grains like rice.

Some embodiments of the formulation contain carbohydrate inulin and other plant fibres. Some embodiments contain myo- and d-Chiro-inositol, folic acid, about 25 vitamins and mineral ingredients and a host of salts/compounds of minerals naturally present and required for healthy human body.

The pea protein powder (concentrate and isolate) which is the second major constituent (>40%) of the disclosed formulations is believed to act as a facilitator or transporter/carrier for the myo-inositol and its isomer d-chiro inositol that renders a synergistic influence on their overall ability to treat of PCOS in women without causing any adverse effects. Table 1 provides a representative composition of the disclosed formulations.

Some embodiments provide a well-defined formulation containing fixed amounts of energy supplying leguminous and non-leguminous plant proteins derived from peas and rice that are wholesome and muscle energy suppliers and are also free from contaminants like saturated fatty acids, cholesterols and residual hormones normally associated with animal proteins. The plant proteins derived from soya and pea-nuts that may contain allergens are specifically excepted. Some embodiments also contain carbohydrates and plant fibres and a well defined proportion of vitamins (A, $B_{1\ to\ 6}$; $B_{12}$ and C); vitamin like substances such as biotin, myo-inositol and its isomer d-chiro inositol; folic acid, a host of several minerals (Ca, Cr, Fe, K, Mg, Mn, Na and Zn) in their various chemical forms and; essential amino acids like L-Glutamine, L-Lysine, and L-Taurine.

Disclosure provides a nutraceutical composition having a protein and an inositol.

Some embodiments of the nutraceutical composition include folic acid. Some embodiments of the nutraceutical composition include a folate. Some embodiments of the nutraceutical composition include a vitamin or a vitamin like substance. Some embodiments of the nutraceutical composition include a mineral. Some embodiments of the nutraceutical composition include a fiber. Some embodiments of the nutraceutical composition include an essential amino acid. Some embodiments of the nutraceutical composition of protein and inositol further include a component selected from the group consisting of a vitamin, a vitamin like substance, a mineral, a fiber, an essential amino acid, or combinations thereof.

In some embodiments of the nutraceutical composition, the protein is a protein of plant origin, a protein of animal origin or combinations thereof.

In some embodiments of the nutraceutical composition the protein of plant origin is a pea protein, a rice protein or combinations thereof.

In some embodiments of the nutraceutical composition the inositol is selected in the group consisting of myoinositol, d-chiro inositol or combinations thereof.

In some embodiments of the nutraceutical composition, the vitamin is selected from the group consisting of vitamin A, vitamin B1, vitamin B2, vitamin B3, vitamin B4, vitamin B5, vitamin B6, vitamin C, vitamin D or combinations thereof.

In some embodiments of the nutraceutical composition, the vitamin like substance is selected from the group consisting of biotin, folic acid or combinations thereof.

Some embodiments of the nutraceutical composition include a dose of a vitamin or vitamin like substance at a dosage as per recommendation by the Indian council of Medical Research for a healthy normal person. In some embodiments the healthy normal person is a woman of post-puberty age.

In some embodiments of the nutraceutical composition the mineral is selected from the group consisting of calcium, chromium, iron, potassium, magnesium, manganese, sodium, zinc, or combinations thereof. In some embodiments of the nutraceutical composition, a chemical form of the mineral is selected from the group consisting of chloride, sulfate, carbonate, or combinations thereof. In some embodiments of the nutraceutical formulation, a dose of the mineral is as per recommendation by the Indian council of Medical Research for a healthy normal person. In some embodiments the healthy normal person is a woman of post-puberty age.

In some embodiments of the nutraceutical composition the fiber is inulin. In some embodiments, the protein extract could also provide fiber.

In some embodiments of the nutraceutical composition the essential amino acid is selected from the group consisting of L-glutamine, L-lysine, L-taurine or combinations thereof. In some embodiments of the nutraceutical composition a dose of the essential amino acid is as per recommendation by the Indian council of Medical Research for a healthy normal person. In some embodiments the healthy normal person is a woman of post-puberty age.

In some embodiments, a dose of the vitamin, vitamin like substance or amino acid is as per values recommended by the Indian Council of Medical Research for a woman of post-puberty age.

In some embodiments, the nutraceutical composition includes:
 about 10% to about 43.5% protein;
 about 10% to about 65% plant fiber;
 about 1% to about 3% inositol;
 less than about 1% vitamins; and
 less than about 1% minerals.

In some embodiments, the nutraceutical composition includes:
 about 43.5% protein;
 about 65% plant fiber;
 about 2% inositol;
 about 1% vitamins; and
 about 0% minerals.

Some embodiments provided a method of treating insulin resistance diseases by administering the disclosed nutraceutical composition to a subject in need thereof.

In some embodiments of the method of treating insulin resistance diseases, the insulin resistance disease is selected from the group consisting of polycystic ovarian syndrome, diabetes, arthritis hypertension and endothelial dysfunction, hyperlipidemia, atherosclerotic heart disease, obesity, peripheral artery disease, type A syndrome, type B syndrome, Acanthosis *Nigricans*, dyslipidemia or cardiovascular conditions.

In some embodiments of the method of treating insulin resistance diseases, a symptom of the poly cystic ovarian syndrome is selected from the group consisting of irregular or missing menstrual cycle, infertility, excess unwanted body or facial hair growth, thinning of hair on the scalp, weight gain around the waist, skin tags, skin darkening, appearance of acne or combinations thereof.

In a preliminary trial of large cohort comprising of about 1000 women in their post-puberty age with various symptoms of PCOS coming from urban background of Mumbai, Pune, New Delhi and Ahmadabad were treated with the disclosed formulations. The results revealed that over 90 percent of them reported partial and/or complete cure of menstrual irregularities and in effect ovulation. The subjects did not mention any adverse effects of the formulations to the treating physicians.

In an infertility clinical trial spread over one year, nine successful pregnancies were noted out of the 12 women undergoing treatment with the disclosed nutraceutical formulations.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

Example 1

A blend of protein, myo-inositol, d-chiro inositol and several other vitamin and mineral ingredients as listed in Table 1 were prepared. In 20 gm of the blend formulation, a mix of pea and rice protein was about 8.8 gm, fiber other than inulin was about 7.6 gm, and the vitamins mineral mixture was about 3.6 gm. This corresponded to about less than 43.5% total protein (mixture of pea and rice protein), less than about 65% dietary plant fibers. The amount of ingredients such as myo-inositol (2 gm in 20 gm of nutraceutical formulation) and d-chiro inositol is listed in Table 1. Vitamins and minerals in the formulation are listed in Table 1, and the corresponding Recommended Daily Allowance (RDA) in percentages of vitamins and minerals as per guidance of Indian Council of Medical Research (ICMR) for healthy women is also provided.

TABLE 1

Approximate Composition of 20 gm of nutraceutical formulation.

| Material or Ingredient | Amount | % RDA |
|---|---|---|
| Pea and rice protein | 8.8 gm | |
| Dietary plant fiber | 7.6 gm | |
| Myo-inositol | 2 gm | NA |
| D-Chiro inositol | 0.05 gm | NA |
| Inulin | 1.3 gm | NA |
| Vit. C | 40 mg | 100 |
| Calcium Carbonate | 40 mg | 2.6 |
| Magnesium Sulfate | 40 mg | 2.37 |
| Zinc Sulfate | 30 mg | 100 |
| Vit $B_5$ | 15 mg | |
| Sod. Chloride | 10 mg | 0.18 |
| Potassium Chloride | 10 mg | 0.10 |
| Vit.$B_3$ | 2.2 mg | 12.2 |
| Ferrous Fumerate | 2 mg | 3.88 |
| Vit. $B_6$ | 2 mg | 100 |
| Vit $B_2$ | 1.6 mg | 100 |
| Vit.$B_1$ | 1.4 mg | 100 |
| Manganese Sulfate | 0.6 mg | 4.36 |
| Folic Acid | 0.2 mg | 100 |
| Vit.A (acetate) | 0.02 mg | 3.33 |
| Sod. Selenite | 40 mg | 45.56 |
| Biotin | 30 mg | ** |
| Chromium Picolinate | 2 mcg | 0.12 |
| Potassium Iodie | 2 mcg | 1.01 |
| Vit. $B_{12}$ | 1 mcg | 100 |
| L-Glutamine | 0.85 mcg | NA |
| L-Taurine | 0.71 mcg | NA |
| L-Lysine | 0.56 mcg | NA |
| Vit.D | 400 I.U. | NA |

Example 2

132 patients who were diagnosed with PCOS symptoms over a two and half month time period were studied. The patients were administered the plant protein-based powder formulation as described in Example 1, which had protein, inositol, fiber besides other ingredients such as vitamins and minerals. A dose of 4 scoops of the nutraceutical formulation mixed in water was given twice daily (once before breakfast and once before dinner) for first month. If improvement in PCOS symptoms was found, then the dosage was lowered to 4 scoops of formulation mixed in water and given once daily (before breakfast). Study monitored improvement in features of PCOS such as acne, hirsutism, menstrual irregularities and blood sugar levels.

At the start of study, we performed basic physical examination of the patients by recording features such as androgen excess, and blood test for measuring fasting blood sugar level, follicular stimulating hormone (FSH), lutenizing hormone (LH), (AMH) and testosterone levels. Patients were counseled for lifestyle modification and diet management. All patients consumed the formulation for two months and at monthly intervals the following parameters were retested: menstrual pattern, acne, hirsutism and blood sugar.

Each unit dose provides about 20 gm of oral dosage of nutraceutical formulation having about 2 gm of myoinositol. When consuming two doses of 20 gm each dose of the nutraceutical formulation, patient received 4 grams of myoinositol per day, which is the minimum recommended dosage for treatment of PCOS. ((*Int J Endocrinol.* 2016; 2016: 9537632; Published online 2016 Aug. 23. doi: 10.1155/2016/9537632; PMCID: PMC5011528; PMID: 27642297, Myoinositol as a Safe and Alternative Approach in the Treatment of Infertile PCOS Women: A German Observational Study, Pedro-Antonio Regidor and Adolf Eduard Schindler.).

In our earlier unpublished studies, when only protein was administered to subjects, we found some improvements in symptoms but almost no cases (<2%) of restoration of ovulation. We did not find any published studies that PCOS was reversed by administration of protein alone. Other researchers had found that when inositol alone was administered about 62% of patients showed improvement in ovulation (*Gynecol Endocrinol.* 2015 Feb.; 31(2):131-5. doi: 10.3109/09513590.2014.964640, Epub 2014 Sep. 26, Zdravko Kanenov 1, Georgi Kolarov, Antoaneta Gateva, Gianfranco Carlomagno, Alessandro) Genazzani).

Other studies found that administering inositol and folic acid resulted in about 70% restoration of ovulation (*Int J Endocrinol.* 2016; 2016: 9537632, Published online 2016 Aug. 23. doi: 10.1155/2016/9537632, PMCID: PMC5011528, PMID: 27642297 Myoinositol as a Safe and Alternative Approach in the Treatment of Infertile PCOS Women: A German Observational Study, Pedro-Antonio Regidor and Adolf Eduard Schindler.).

TABLE 2

Improvement in PCOS symptoms after 2 months of treatment with nutraceutical formulation.
Total no of patients-132

| Symptoms | no of patients with problems | improvement in % of patients after 2 months |
|---|---|---|
| Ovulation | 52 | 100 |
| Acne | 89 | 20 |
| Hirsutism | 78 | 12.8 |
| Glucose levels | 90 | 36 |

Our results showed that the nutraceutical formulation which included plant protein, inositols, folic acid, and other vitamins and minerals, there was almost about 100% restoration of ovulation as per study done in a hospital. After 2 months of study protocol, about 20% of subjects showed improvement in acne, whereas after 3 to 4 months of treatment, about 90% of subjects showed improvement in acne. After 2 months of study protocol, 12.8% of subjects showed improvement in hirsutism, whereas after 3 to 4 months of study duration, about 90% of subjects showed improvement in hirsutism. Blood glucose levels was improved in about 36% of subjects after 2 months of treatment.

Our nutraceutical formulation promoted normal hormone and lipid levels for regular menstrual cycles, improved egg quality, increased SHBG (Sex hormone binding globulin) levels and thereby decreased testosterone levels, improved insulin sensitivity, decreased LH levels, effectively managed hirsutism, induced ovulation and prevented gestational diabetes. Our study protocol was easy to follow for patients as all the ingredients were premixed in the nutraceutical formulation for consumption.

Example 3

A small three-month therapeutic clinical trial with the nutraceutical formulation was conducted on 12 infertile women in child bearing age in a small town of Panvel, near Mumbai, India with the following protocol.
 (i) $1^{st}$ month—a 20 gm dosage of nutraceutical formulation of Example 1 was given twice daily first given soon after the breakfast (Or replacing the breakfast altogether in obese women) and the second dose given before dinner.

(ii) 2$^{nd}$ and 3$^{rd}$ Month—If symptoms were under control 20 gm nutraceutical formulation was given once a Day after breakfast (Or totally replacing the breakfast for the obese women).

The results showed that all patients who wanted to become pregnant, namely 9 women of (75%) the group receiving the treatment, had successfully conceived within one year without any untoward complications relating to the treatment. The 3 who did not become pregnant were not attempting pregnancy. So in effect, the treatment protocol resulted in 100% fertility in women who were treated and wanted to become pregnant.

Physician's Further Feedback in general:
(i) Most PCOS Symptoms were controlled after 1 month of treatment which could not be achieved with 6 months of treatment with myo-inositol alone.
(ii) PCOS remained under control in the 3 months schedule of treatment without any relapse on follow-up for 1 year.

Therefore, the results of the infertility study show that the ingredients of the nutraceutical formulation acted synergistically to reverse infertility in 100% of the patients and led to reversal of PCOS symptoms, whereas administration of inositol alone was not as effective as the combination formulation having proteins, myo-inositol, fiber, and other ingredients as in the formulation as described in Example 1.

Other modifications and variations to the invention will be apparent to those skilled in the art from the foregoing disclosure and teachings. Thus, while only certain embodiments have been specifically described herein, it will be apparent that numerous modifications may be made thereto without departing from the spirit and scope of the invention.

What is claimed is:

1. A method of treating polycystic ovarian syndrome comprising administering 20 grams of a nutraceutical composition twice a day for two months to a subject in need thereof,
wherein the nutraceutical composition comprises a protein of plant origin, and an inositol, and wherein about 20 grams of the nutraceutical composition comprises:
about 8.8 grams of a combination of pea protein and rice protein,
about 7.6 grams of dietary fiber,
about 2 grams of myo-inositol;
about 0.05 grams of D-chiro inositol;
about 1.3 grams of inulin;
about 40 mg of Vitamin C;
about 40 mg of Calcium Carbonate;
about 40 mg of Magnesium Sulfate;
about 30 mg of Zinc Sulfate;
about 15 mg of Vit B$_5$;
about 10 mg of sodium chloride;
about 10 mg of potassium chloride;
about 2.2 mg of Vit. B$_3$;
about 1.6 mg of Vit B$_2$;
about 0.6 mg of manganese sulfate;
about 0.2 mg of folic acid;
about 0.02 mg of Vitamin A;
about 40 mg of sodium selenite;
about 30 mg of biotin;
about 2 mcg of chromium picolinate;
about 2 mcg of potassium iodide;
about 1 mcg of Vit. B$_{12}$;
about 0.85 mcg of L-glutamine;
about 0.71 mcg of L-Taurine;
about 0.56 mcg of L-lysine;
about 400 I.U. of Vitamin D,
and
wherein a symptom of poly cystic ovarian syndrome is selected from the group consisting of irregular or missing menstrual cycle, infertility, excess body or facial hair growth, thinning of hair on the scalp, weight gain around the waist, skin tags, skin darkening, appearance of acne, and combinations thereof.

2. The method of treating polycystic ovarian syndrome of claim 1, wherein the nutraceutical composition further comprises a folate.

3. The method of treating polycystic ovarian syndrome of claim 1, further comprising vitamin B$_4$.

4. The method of treating polycystic ovarian syndrome of claim 1, comprising a mineral selected from the group consisting of calcium, chromium, iron, potassium, magnesium, manganese, sodium, zinc, and combinations thereof, and wherein a chemical form of the mineral is selected from the group consisting of chloride, sulfate, carbonate, and combinations thereof.

* * * * *